(12) United States Patent
Zocher et al.

(10) Patent No.: US 6,828,115 B1
(45) Date of Patent: Dec. 7, 2004

(54) EPOXIDE HYDROLASES FROM STREPTOMYCES

(75) Inventors: Frank Zocher, Stuttgart (DE); Markus Enzelberger, Stuttgart (DE); Rolf D. Schmid, Stuttgart (DE); Wolfgang Wohlleben, Tübingen (DE); Bernhard Hauer, Fussgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 96 days.

(21) Appl. No.: 10/031,702

(22) PCT Filed: Jul. 26, 2000

(86) PCT No.: PCT/EP00/07211

§ 371 (c)(1),
(2), (4) Date: Jan. 23, 2002

(87) PCT Pub. No.: WO10/07623

PCT Pub. Date: Feb. 1, 2001

(30) Foreign Application Priority Data

Jul. 27, 1999 (DE) .......................................... 199 35 113

(51) Int. Cl.[7] .............................. C12Q 1/34; C12N 1/14; C12P 17/02; C12P 7/18
(52) U.S. Cl. ......................... 435/18; 435/145; 435/123; 435/158; 435/280
(58) Field of Search .......................... 435/195, 18, 158, 435/123, 253.5, 280, 253.4

(56) References Cited

PUBLICATIONS

Nells, H.J.C.F, et al. (1982) Anal. Chem. 54, 213–216.*
Grogan et al. "Novel aliphatic epoxied hydrolase activities from dematiaceous fungi" FEMS Microbiology Letters vol. 141 (1996) pp. 239–243.
Kroutil et al. "Deracemization of (±)–cis–2,3–Epoxyhetane via Enantioconvergent Biocatalytic Hydrolysis using *Nocardia* EH1–Epoxide Hydrolase" Tetrahedron Letters vol. 37 No. 46 (1996) pp. 8379–8382.
Misawa et al. Characterisation of a catabolic epoxied hydrolase from a *Corynebacterium* sp. Eur. J. Biochem. vol. 253 (1998) pp. 173–183.
Rink et al. "Primary Structure and Catalytic Mechanism of the Epoxide Hydrolase fro *Agrobacterium radiobacter* AD1*" J. Biological Chemistry vol. 272, No. 23 (1997) pp. 14650–14657.
Mischitz et al. "Isolation of a Highly Enantioselective Epoxide Hydrolase from *Rhodococcus* sp. NCIMB 11216" Biotechnology Letters vol. 17 (1995) pp. 893–898.
Kroutil et al. "Purification and characterization of a highly selective epoxied hydrolase from *Nocardia* sp. EH1" J. of Biotechnology vol. 61, (1998) pp. 143–150.
Lutz–Wahl et al. "Stereo– and Regioselective Hydroxylation of α–Ionone by Streptmyces Strains" Applied and Environmental Microbiology 64(10) (1998), pp. 3878–3881.
Zocher et al. "A colorimetric assay suitable for screening epoxied hydrolase activity" Analytica Chimica Acta vol. 391 (1999) pp. 345–351.
Weijers et al. "Epoxide hydrolases from yeasts and other sources: versatile tools in biocatalysts" J. of Molecular Catalysts B: Enzymatic vol. 6, (1999) pp. 199–214.
Zocher et al. "Epoxide hydrolase activity of Streptomyces strains" J. of Biotechnology vol. 77 (2000) pp. 287–292.

\* cited by examiner

*Primary Examiner*—Charles L. Patterson, Jr.
(74) *Attorney, Agent, or Firm*—Keil & Weinkauf

(57) ABSTRACT

A description is given of epoxide hydrolases from bacteria of the genus *Streptomyces*, a novel process for the enzymatic separation of epoxide enantiomeric mixtures, of a novel detection method for epoxide hydrolase activity, a screening method for detecting epoxide hydrolase activity and the use of bacteria of the genus *Streptomyces* and of the resultant epoxide hydrolases for enantioselective epoxide hydrolysis.

Figure 1:
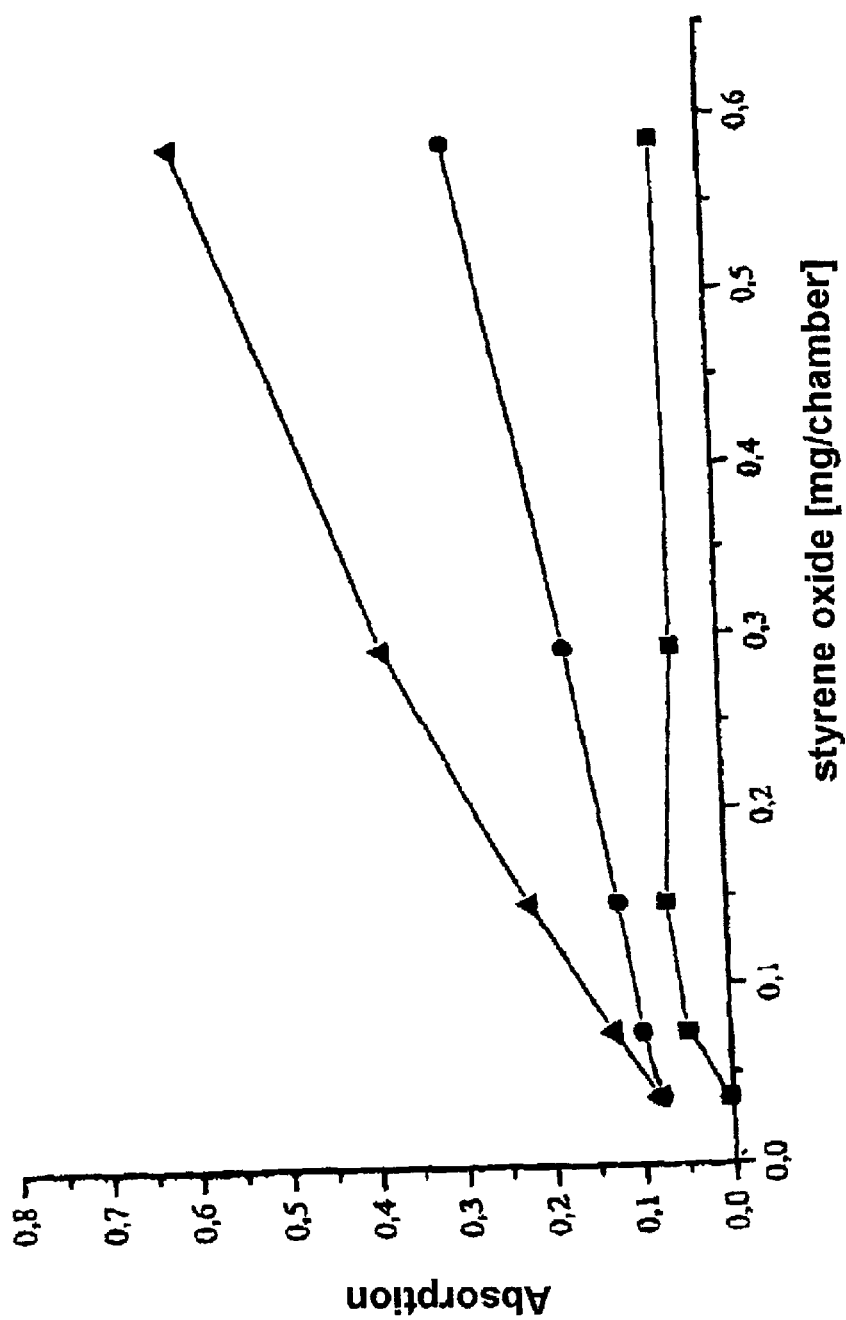

17 Claims, 3 Drawing Sheets

EPOXIDE HYDROLASES FROM STREPTOMYCES

The invention relates to improved epoxide hydrolases which can be isolated from bacteria of the genus *Streptomyces*, a novel process for the enzymatic separation of epoxide enantiomer mixtures, a novel detection method for epoxide hydrolase activity, a screening method for detecting epoxide hydrolase activity and the use of bacteria of the genus *Streptomyces* and the resultant epoxide hydrolases for enantioselective epoxide hydrolysis.

The increasing importance of enantiomerically pure compounds, especially in the pharmaceutical and agrochemical industries, requires reliable and economic access to optically active substances. To prepare enantiomerically pure diols and epoxides, a number of methods are available.

In asymmetric chemical synthesis of epoxides, synthesis starts from a prochiral compound. By using a chiral reagent, for example a chiral peracid, a chiral dioxirane or oxaziridine or a chiral borate, a chiral auxiliary or a chiral, metallic or nonmetallic catalyst, a chiral epoxide is formed. The best known pathway for synthesizing chiral epoxides is the Sharpless epoxidation of alkenols, for example allyl alcohols, with hydroperoxides in the presence of transition metal catalysts.

Preparation of enantiomerically pure diols by a biochemical pathway is also known. Microorganisms having epoxide hydrolase activity catalyze the regiospecific and enantiospecific hydrolysis of epoxides. They cleave the ether bond in epoxides, forming diols. Some bacterial strains have already been described which enable a broad selection of racemic epoxides to be hydrolyzed enantioselectively. However, the number of known epoxide hydrolases and their application to organic synthesis has been restricted to date. Known strains having epoxide hydrolase activity are, for example, *Aspergillus niger* LCP521, *Bacillus sulfurescent* ATCC 7159, *Rhodococcus* species NCIMB 11216 and others.

However, the known strains having epoxide hydrolase activity often have a restricted substrate spectrum and low reaction rates. Also, the enantioselectivities which can be achieved using these strains are frequently too low [Grogan, G., et al., FEMS Microbiology Lett. 141 (1996), 239–243; Kroutil, W., et al., Tetrahedron Lett. (1996), 8379–83821. The known strains are difficult to manipulate genetically and some are difficult to culture. Therefore, to date, only two epoxide hydrolases are available in recombinant form in *E. coli* [*Corynebacterium sp.* C12, (Misawa, E., et al., Eur. J. Biochem. 253 (1998), 173–183) and *Agrobacterium radiobacter* AD1 (Rink, R., et al., J. Biol. Chem. 272 (1997), 14650–14657)]. Even purification of the epoxide hydrolases obtained from the microorganisms has to date only been described for *Rhodococcus species* NCIMB 11216 [Faber, K., et al., Biotechnology Lett. 17 (1995), 893–898] and *Norcardia* EH 1 [Kroutil, W., et al J. Biotechnol. 61 (1998), 143–150]. This was highly complex in both cases. The enrichment of epoxide hydrolases from *Corynebacterium sp.* C12 is described by Misawa, E., et al., Eur. J. Biochem. 253, (1998) 173–183.

In addition, the search for novel epoxide hydrolase-containing microorganisms is made difficult owing to the fact that screening for novel epoxide-hydrolase-producing microorganisms, for example in collections of microbiological strains, has hitherto been highly time-consuming. This is due to the fact that, for screening, usually methods are used in which the individual batches must be worked up and analyzed individually by gas chromatography or liquid chromatography.

It is a first object of the invention, therefore, to provide novel epoxide hydrolases having an expanded substrate spectrum and/or improved reactivity and/or improved enantioselectivity. In addition, the novel epoxide hydrolases should be more readily accessible, in particular, because they can be isolated from nonpathogenic organisms which can be readily cultured, and, in addition, if appropriate are readily accessible to methods of molecular biology.

It is a second object of the invention to provide a method for the more rapid and simpler detection of epoxide hydrolase, which should also allow improved screening for epoxide-hydrolase-producing micro-organisms.

It is a third object of the invention to provide an improved biochemical process for separating epoxide enantiomer mixtures and thus an improved process for the enantioselective reaction of epoxides which permits a simpler route to the enantiomerically pure diols and/or epoxides.

It is a fourth object of the invention to provide novel epoxide-hydrolase-producing microorganisms.

We have found that the above first object is achieved, surprisingly, by providing epoxide hydrolases (E.C. 3.3.2.3) from microorganisms of the genus *Streptomyces*. Epoxide hydrolase activity has not previously been described in microorganisms of this genus.

The inventive epoxide hydrolases have at least one of the following advantageous properties, compared with previously known epoxide hydrolases:
 improved enantioselectivity in the resolution of enantiomeric epoxides;
 improved (expanded) substrate spectrum;
 improved reactivity;
 enhanced accessibility to methods of molecular biology;
 improved biochemical accessibility because the microorganisms are easier to culture.

For the purposes of the invention, "improved enantioselectivity" is when, for substantially the same conversion rate, a higher enantiomeric excess is achievable.

For the purposes of the invention, an "expanded substrate spectrum" is that racemic mixtures of a plurality of epoxides are converted.

For the purposes of the invention, an "improved reactivity" is that the reaction takes place with a higher space-time yield.

The invention relates in particular to those epoxide hydrolases from *Streptomyces* that have at least one of the following properties:
 a) hydrolytic epoxide cleavage of a styrene oxide, for example styrene oxide or a derivative thereof which is monosubstituted or polysubstituted on the phenyl ring or epoxide ring, such as in particular a styrene oxide which is monosubstituted in the meta or para position by nitro or halogen, in particular chlorine or bromine, and at least one further compound selected from the group consisting of ethyl 3-phenylglycidate, n-hexane-1,2-oxide, n-decane-1,2-oxide and indene oxide, which can be unsubstituted or monosubstituted or polysubstituted by substituents preferably in accordance with the above definition;
 b) conversion of a racemate of styrene oxide with an enantioselectivity E>2, for example $\geq$10, for instance from 10 to 100, to give (S)-phenyl-1,2-ethanol according to the reaction equation (A) given below, this conversion being able to be carried out using whole cells or a cell homogenate or an enriched or purified enzyme preparation, and preferably taking place in the presence of a cosolvent, for example from 5 to 10% (v/v) DMSO.

According to a preferred embodiment, the epoxide hydrolases provided are those which can be isolated from bacteria of the genus *Streptomyces*, in particular from the species *S. griseus, S. thermovulgaris, S. antibioticus, S. arenae* and *S. fradiae*, preferably from the strains *Streptomyces griseus* (DSM 40236 and DSM 13447), *Streptomyces thermovulgaris* (DSM 4044 and DSM 13448), *Streptomyces arenae* Tü (DSM 40737 and DSM 12134) *Streptomyces antibioticus* Tü4 (DSM 12925) or *Streptomyces fradiae* Tü27 (DSM 12131).

Particular preference is given to the epoxide hydrolase which can be isolated from *Streptomyces antibioticus* Tü4 (DSM 12925). This enzyme is characterized by its pronounced enantioselectivity and the conversion of (R/S)-styrene oxide (I) according to the following reaction equation (A)

Reaction equation (A):

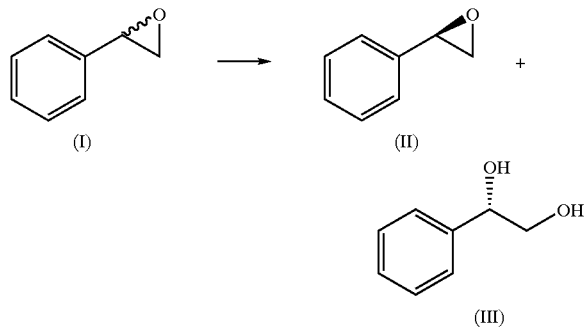

to (S)-phenyl-1,2-ethanediol (III), with the non-hydrolysis of (R)-styrene oxide (II). Thus this enzyme in a reaction medium containing 10% (v/v) DMSO as solubilizer, catalyzes the above conversion at an enantioselectivity of E=13 and an enantiomeric excess ee[%]=99 for (II) and ee[%]=14 for (III).

Isolation of the enzyme is described in more detail in the examples. Unless stated otherwise, the enzyme is enriched using standard biochemical methods, for example as described by T. G. Cooper in Biochemische Arbeitsmethoden [Biochemical methods], Verlag Walter de Gruyter, Berlin, N.Y., (1981). Suitable methods, for example, are purification methods such as precipitation, for example using ammonium sulfate, ion-exchange chromatography, gel chromatography, affinity chromatography, for example immunoaffinity chromatography, and isoelectric focusing, and combinations of these methods.

The invention also relates to a novel *Streptomyces* strain having the designation *Streptomyces antibioticus* Tü4, deposited at the DSMZ under the Deposit Number DSM 12925 and variants and mutants of this strain.

The invention also relates to functional analogs of the inventively prepared enzymes, such as variants, alleles and mutants, that have epoxide hydrolase activity and, preferably, have at least one of the above-mentioned advantageous properties.

We have found that the above second object was achieved, surprisingly, by providing an optical method of detection for epoxide hydrolase, which comprises
a) incubating an analyte, for example a microorganism culture, in which epoxide hydrolase activity is suspected with an epoxide-containing substrate for the epoxide hydrolase under reaction conditions;
b) chemically reacting unreacted epoxide with 4-nitrobenzylpyridine (NBP), forming a pigment absorbing at 560 nm; and
c) analyzing the solution from step b) for decrease in pigment concentration, relative to an epoxide-hydrolase-free control solution.

The inventive detection method can be carried out qualitatively, for example as a spot test, or quantitatively. In the quantitative method, the relative decrease in pigment concentration is first determined quantitatively, for example photometrically by determining absorption at 560 nm, and the epoxide hydrolase activity in the analyte is determined therefrom.

Suitable analytes are in principle microorganisms per se, for example samples from a freshly taken culture of a bacterium, cell homogenates thereof or fractions of these cell homogenates after purification. Preferably, the test is carried out using whole cells or after digestion of the cells, for example using ultrasound or lysozyme.

For example, the method is applicable to detecting epoxide hydrolase in bacteria of the genus *Streptomyces*.

Preferably, the detection method is carried out in such a manner that a sample is withdrawn from a freshly taken culture of the microorganism, this is disrupted, freed from cell fragments and an epoxide comprising a substrate for the enzyme to be tested is added and mixed. If required, the reaction conditions can be optimized in the solution by customary measures, for example by adding buffer, adjusting the reaction temperature and the like. Preferably, to improve the solubility of the epoxide in the aqueous reaction medium, a cosolvent is used. Suitable cosolvents are, for example, dimethyl sulfoxide (DMSO), dimethylformamide (DMF), ethanol or acetone. Optimum reaction conditions for epoxide hydrolases from *Streptomyces* comprise:

Reaction medium: Sodium phosphate buffer pH 8.0, 0.1 M, 10% (v/v) DMSO
pH range: 6–8
Temperature: 30–37° C.
Reaction time: 2–20 hours
Substrate concentration: from 0.1 to 0.8 molar The substrate preferably used is styrene oxide, 3-phenylglycidate, hexane-1, 2-oxide, decane-1, 2-oxide and/or indene oxide in enantiomerically pure form or as enantiomeric mixture.

To develop the color reaction, the pH is then adjusted by adding a base, for example triethylamine. NBP is then added, for example at a concentration in the range from about 3 to 10%, preferably about 5% (w/v) in methoxyethanol. As solubilizer for the pigment formed, for example, triethylene glycol dimethyl ether is added in sufficient quantity. The solution is finally incubated at from about 35 to 45° C., preferably 39° C., and the absorption is then determined at 560 nm, preferably against a reference at 650 nm. From comparison with an enzyme-free control solution, the decrease in absorption and thus the decrease in epoxide can be determined quantitatively.

The invention also relates to screening methods for detecting microorganisms having epoxide hydrolase activity and/or having the ability to hydrolyze epoxides enantioselectively, comprising the above described detection method. This is particularly suitable for systematic study of strain collections or mutant banks, generated by "directed evolution", for epoxide hydrolase activity.

We have found that the above third object was achieved, surprisingly, by providing a process for separating epoxide enantiomer mixtures which comprises
a) incubating an epoxide enantiomer mixture, which comprises an epoxide hydrolase substrate, with an inventive epoxide hydrolase, a microorganism of the genus *Streptomyces*, an epoxide-hydrolase-containing homogenate thereof or a fraction of this homogenate under reaction conditions;

b) reacting the enantiomer mixture, preferably to achieve a 50% conversion rate; and c) separating the enantiomer remaining in the reaction mixture from the conversion product and purifying the essentially enantiomerically pure reaction product and/or the essentially enantiomerically pure starting material remaining.

Preferably, enantiomer mixtures of one of the following epoxides is converted: styrene oxide, 3-phenyl-glycidate, hexane-1,2-oxide, decane-1,2-oxide and indene oxide or substituted analogs of these oxides in accordance with the above definition.

The invention further relates to a process for producing epoxide hydrolases (E.C. 3.3.2.3), which comprises a) producing a cell homogenate from a culture of a microorganism of the genus *Streptomyces*;

b) fractionating the homogenate, the resultant fractions being tested for epoxide hydrolase activity, preferably using a detection method based on the color reaction of unreacted epoxide with NBP according to the above definition; and c) combining fractions having epoxide hydrolase activity and if appropriate further fractionating.

The invention finally relates to the use of an inventive epoxide hydrolase, a microorganism of the genus *Streptomyces*, an epoxidehydrolase-containing homogenate thereof or a fraction of this homogenate for the enantioselective hydrolysis of epoxides.

The invention is described in more detail by the examples below and with reference to the accompanying figures. In the drawings:

FIG. 1 shows results of measurements of pigment formation from NBP and epoxide at various styrene oxide concentrations. The change in absorption in solutions in the presence of *E. coli* DH5a by the NBP assay (black circles), without *E. coli* DH5a cell and without NBP (black squares) and with cell lysate of *E. coli* DH5a by the NPB assay (black triangles) are plotted, in each case after 45 minutes at the specified styrene oxide concentrations.

Figure 2:
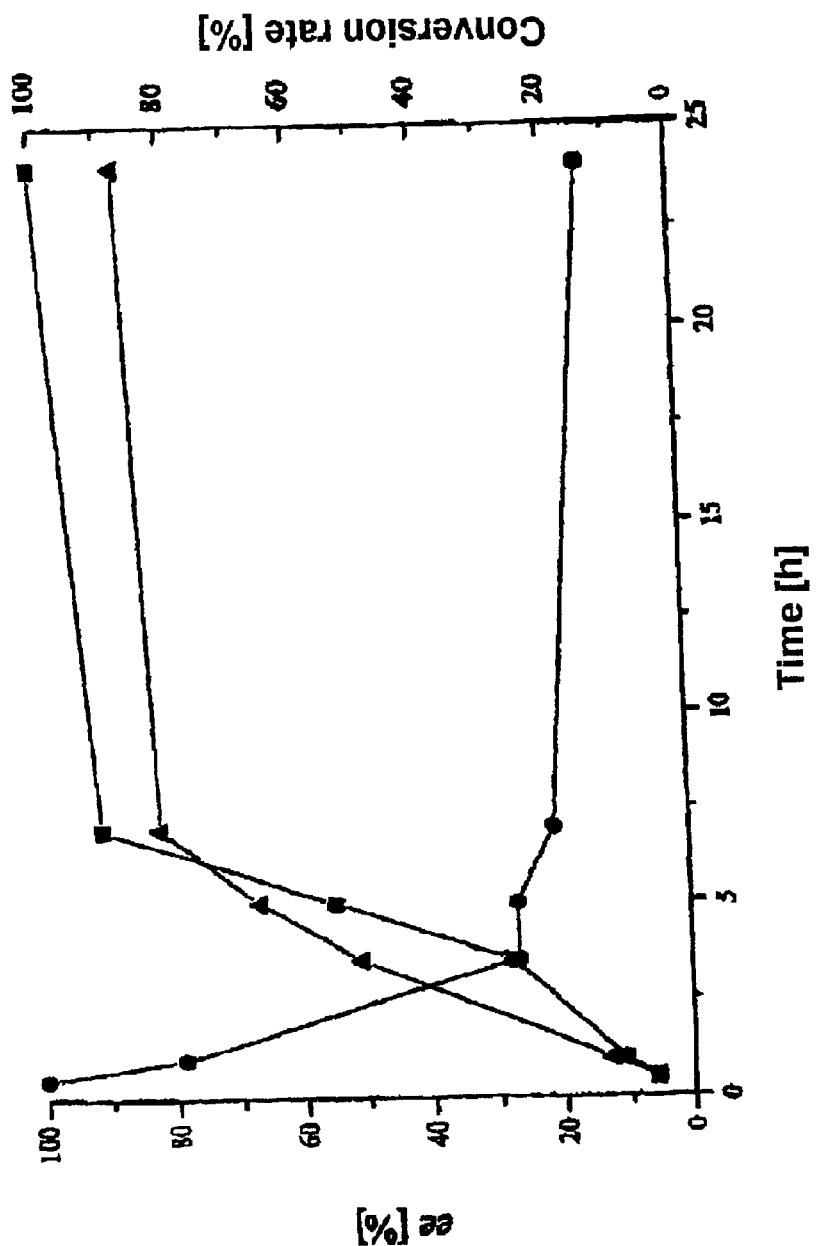
Figure 3:
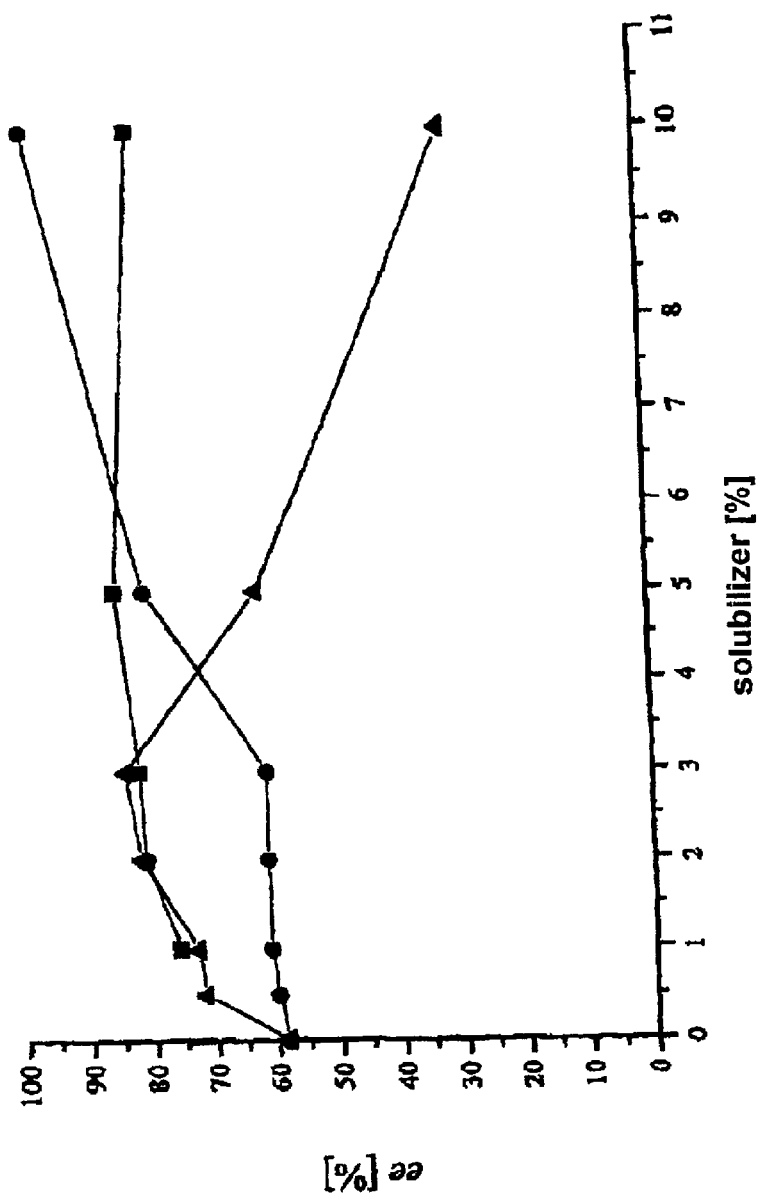

FIG. 2 shows the time course of racemate resolution of styrene oxide by the epoxide hydrolase from *S. antibioticus* Tü4 (DSM 12925). ee[%] (R)-styrene oxide (black squares); ee[%] (S)-phenyl-l, 2-ethanediol (black circles); conversion rate [%] (black triangles);

FIG. 3 shows the effect of various cosolvents on the hydrolysis of styrene oxide by epoxide hydrolase from *S. antibioticus* Tü4 (DSM 12925); ee[%] (R)-styrene oxide is plotted as a function of cosolvent concentration (%(v/v)); acetone (black squares); DMSO (black circles); DMF (black triangles).

Example 1

Validation of a test system for epoxide hydrolase a) Styrene oxide as substrate

An epoxide hydrolase-free organism (*E. coli* DH5a) was cultured in 2 ml cultures and disrupted. 100 µl aliquots of the resultant cell lysates were distributed over 4 recesses of a microtitre plate. To the cell lysate was added 50 µl of acetone containing various amounts of styrene oxide (1.3 mol/l (stock solution)., 0.65 mol/l, 0.32 mol/l, 0.16 mol/l, 0.08 mol/l). The solution was incubated at 30° C. for 2 hours. After adding 25 µl of triethylamine (TE), 50 µl of p-nitrobenzylpyridine (NBP, 5% by volume) and 50 µl of triethylene glycol dimethyl ether, it was again incubated at 39° C. for 45 minutes and then the absorption was measured at 560 nm against a reference of 650 nm.

The results are shown in FIG. 1. The absorption increased linearly with the amount of styrene oxide used. Therefore, the decrease in absorption indicates the presence of an epoxide hydrolase activity.

b) 3-Phenylglycidate as substrate

Example 1a) was repeated, except that the substrate used was 3-phenylglycidate. In this case also, there was a linear relationship between absorption and the remaining amount of unhydrolyzed epoxide.

c) Hexane-1,2-oxide as substrate

Example 1a) was repeated, except that the substrate used was hexane-1,2-oxide. In this case also there was a linear relationship between absorption and the remaining amount of unhydrolyzed epoxide.

d) Indene oxide as substrate

Example 1a) was repeated, except that the substrate used was indene oxide. In this case also there was a linear relationship between absorption and the remaining amount of unhydrolyzed epoxide.

Example 2

Screening various *Streptomyces* strains for epoxide hydrolase activity using styrene oxide as substrate In a similar manner to Example 1, various deposited *Streptomyces* strains were tested, and also, as negative control, a bacterial strain of the genus *Rhodococcus* sp. (NCIMB 11216). The microtitre plate wells which contained the negative control exhibited an intensive color reaction (blue coloration), whereas in wells containing *Streptomyces antibioticus* Tü4 (DSM 12925) and *Streptomyces fradiae* Tü27 (DSM 12131) the highest epoxide hydrolase activity was found (results not shown).

Example 3

Culturing the strain *Streptomyces antibioticus* Tü4

The organism was cultured both in 250 ml shake flasks and in a 30 l fermenter; the pH was not monitored.

a) 250 ml fermentation: the culture time at 30° C. on the 250 ml scale was from 48 to 72 hours.

b) 30 l fermentation: 2 shake flasks each containing 1 l of malt medium [10 g of malt extract, 4 g of yeast, made up to 1 l with tap water and autoclaved, sterile-filtered glucose (4 g/l final concentration) was added after autoclaving] were inoculated with spores of *Streptomyces antibioticus* Tü4; the cultures were then shaken for 48 hours (30° C., 210 rpm). 2 l of this preliminary culture were used to inoculate 20 l of malt medium (addition of 0.5 l of 20% strength by weight glucose solution to 20 l of malt extract/yeast solution), prior homogenization (glass homogenizer, Braun Chemie) being recommended for colony growth as disperse as possible. The culture was stirred for 24 hours at 30° C. in the 30 l fermenter (17 l/min of 02, 200 rpm), then the fermentation was terminated. The cells were centrifuged off at 4000 rpm for 30 minutes and washed with TE buffer (pH 7.3, 1 mmol/l of EDTA. The moist biomass was 318 g. The cells were resuspended in 400 ml of TE buffer (pH 7.3, 1 mmol/l of EDTA).

Example 4

Enrichment of epoxide hydrolase from *S. antibioticus* Tü4 a) Cell disruption:

For the experiments with disrupted cells, the cultured cells were removed by filtration or centrifugation and washed twice with phosphate buffer (0.1 mol/l of NaCl, 10 mmol/l of EDTA). A suspension (10% w/v) was then prepared in the same buffer additionally containing 10 mg/ml of lysozyme. The suspension was incubated for 1 hour at 30° C. and then disrupted twice for 5 minutes each time, with 1 minute in between, with ultrasound (Branson Sonifier W250, output 80 W) in an ice bath. The resultant solution was centrifuged off for 60 minutes at 32 500 g and filtered (0.22 mm Sterivex-GP filter, Millipore)

b) Cell extract workup

A column packed with an anion exchanger (Super Q 650M, Toso Haas, 60 mol volume) was equilibrated with 25 ml of tris/HCl buffer (pH 8.1), and then 15 ml of the crude extract were applied. The column was eluted with 2 mol/l NaCl solution containing the following gradients: 1st gradient: 30 ml NaCl solution (0–12% by weight), 2nd gradient: 60 ml NaCl solution (12–35% by weight), Wash with 25 ml NaCl solution (100% by weight), reequilibration with 60 ml of tris/HCl buffer.

Flow rate: 4 ml/min, fraction size 4 ml. Protein was determined at 280 nm.

Activity of the individual fractions was determined using the NBP assay. For this, 150 $\mu$l from the fractions were added to the wells of a 96-well microtitre plate and the NBP assay was performed as described above using the Biomek 2000 pipetting robot. 50 $\mu$l of acetone solution containing styrene oxide (2.6 mol/l) were used in order to reduce the amount of acetone, since the addition of acetone in an amount which is relatively too large can lead to a decrease in enzyme activity. The rest of the experimental procedure was performed in a similar manner to the procedure described above. In the enrichment, all of the epoxide hydrolase activity was detected in one fraction.

Example 5

Conversion of styrene oxide using epoxide hydrolase from *S. antibioticus* Tü4 a) Reaction procedure

500 $\mu$g of styrene oxide were added to 250 ml of the cell-free extract from Example 4 containing 12.5 ml of DMSO as solubilizer. The mixture was incubated at 30° C. with uniform shaking (250 rpm).

After 24 hours, the reaction was terminated by adding 30 ml of ethyl acetate, and the aqueous phase was extracted. The organic phase was concentrated under reduced pressure. Gas-chromatographic analysis found an enantiomeric excess of the substrate of ($ee_s[\%]$) of 100 and of the product ($ee_p[\%]$) of 14.

The enantiomeric purity of a chiral substance, which occurs in (R)- and (S) forms, is expressed by the parameter ee (enantiomeric excess). This is defined by the following equation:

$$ee[\%]=[(X_A-X_B)/(X_A+X_B)]*100$$

where $X_A$ and $X_B$ are the molar fraction of enantiomer A and B, respectively.

The enantiomeric excesses were analyzed by chiral gas chromatography under the following conditions: 75° C. isothermal, 130 kPa, on an FS-Cyclodex β-I/P CS-fused silica capillary column (CS-Chromatographie Service GmbH, Langerwehe) (H$_2$ carrier gas, split 1:100, 0.25 mm ×50 mm).

The product phenyl-1,-2-ethanediol was analyzed under the following conditions: 140° C. isothermal under otherwise identical conditions.

The enantioselectivity E of an enzymatic reaction is a constant for an enzyme which is independent of substrate concentration and conversion rate and, for an irreversible reaction without product inhibition, may be calculated using the following formula:

$$E=(V_{max}/K_m)_{(R)-Enantiomer}/(V_{max}/K_m)_{S-Enantiomer}=\{ln(1-U)(1-ee_s)]\}/\{1n[(1-U)(1+ee_s)]\}=\{1n[(1-U)(1+ee_p)]\}/\{(1-U)(1-ee_p)]\}$$

where $ee_s$ is the enantiomeric excess of the substrate and $ee_p$ is the enantiomeric excess of the product and the conversion rate U may be calculated from the formula $U=ee_s/(ee_s+ee_p)$.

Evaluation was performed as described by Chen, C. S. et al., (1982) J.Am.Chem.Soc. 104, 7294.

b) Determination of enantioselectivity

To follow the course of the reaction, 1.5 ml lots of the cell-free extract were shaken with 75 ml of DMSO and 7 ml of styrene oxide in sealable 2 ml reaction vessels at 30° C. and extracted with 300 ml of ethyl acetate at predetermined times.

Table 1 shows the results.

TABLE 1

| Time [h] | $ee_s$ [%] | $ee_p$ [%] | Conversion rate [%] |
|---|---|---|---|
| 0.5 | — | — | — |
| 1 | 11 | 66 | 15 |
| 3.5 | 23 | 26 | 47 |
| 5 | 33 | 22 | 59 |
| 7 | 91 | 21 | 82 |
| 24 | 100 | 14 | 87 |

The time course of the reaction is shown in the accompanying FIG. 2.

Example 6

Hydrolysis of styrene oxide by *Streptomyces* strains *S. fradiae* Tü 27 and *S. arenae* Tü 495

Whole cells of a 250 ml culture of the organism were resuspended in 200 ml of sodium phosphate buffer (0.1 M, pH 8). To this were added 500 $\mu$l of styrene oxide and 10% (v/v) of DMSO. The reaction solution was shaken at 30° C. at 210 rpm in a closed conical flask. Samples (1.5 ml) were taken at various time intervals to monitor the course of the reaction, centrifuged at 14000 rpm for 3 minutes and extracted with 300 $\mu$l of diethyl ether. The organic phases were dried using anhydrous sodium sulfate and analyzed by gas chromatography to determine the enantiomeric excess, the conversion rate and the enantioselectivity as described above. The results are summarized in Table 2 below:

TABLE 2

| Strain | Enantiomeric excess $ee_s^a$ [%] | $ee_p^b$ [%] | Conversion rate [%] | Time [h] |
|---|---|---|---|---|
| Tü27 | 70 | 23 | 75 | 48 |
| Tü95 | 52 | 38 | 60 | 24 |

[a] (R)-Styrene oxide
[b] (S)-Phenyl-1,2-ethanediol

Example 7: Effect of cosolvents on styrene oxide hydrolysis.

Example 6 was repeated, but *S. antibioticus* Tü4 was used as the microorganism, and DMSO, DMF or acetone were added to the reaction solutions in various amounts. The results are shown in FIG. 3. 10% DMSO, 5% acetone and 1–3% DMF led to an increase in enantiomeric excess, and thus in enantioselectivity.

Example 7

Hydrolysis of ethyl 3-phenylglycidate (3-PEG) and n-decane-1,2-oxide by epoxide hydrolase from *S. antibioticus* Tü4

Example 5 was repeated, but instead of styrene oxide, 3-PEG or n-decane-1,2-oxide was used as substrate.

a) Conversion of 3-PEG:

In contrast to Example 5, 3-PEG was analyzed gas-chromatographically at 60 kPa, 130° C. (60 min), 180° C. (5 min), 10° C./min b) Conversion of decane-1,2-oxide The decane-1,2-diol formed was derivatized with acetone and p-toluenesulfonic acid as catalyst in ethyl acetate. Isopropylidenedecane-1,2-diol was analyzed at 120° C. under the conditions specified in Example 5.

We claim:

1. An epoxide hydrolase (E.C. 3.3.2.3) from a microorganism of the genus *Streptomyces*.

2. An epoxide hydrolase as claimed in claim 1, having at least one of the following properties:
   a) hydrolytic epoxide cleavage of a styrene oxide and of at least one other compound selected from ethyl 3-phenylglyci-dates, n-hexane-1,2-oxides, n-decane-1, 2-oxides and indene oxides;
   b) conversion of a racemate of styrene oxide with an enantioselectivity E≧2 to give (S)-phenyl-1,2-ethanol.

3. An epoxide hydrolase isolated from bacteria of the genus *Streptomyces* from the species *Streptomyces griseus*, *Streptomyces thermovulgaris*, *Streptomyces antibioticus*, *Streptomyces arenae* and *Streptomyces fradiae*.

4. The epoxide hydrolase of claim 3, wherein the bacteria of the genus *Streptomyces* are selected from the strains *Streptomyces griseus* (DSM 40236 and DSM 13447), *Streptomyces thermovulgaris* (DSM 40444 and DSM 13448), *Streptomyces antibioticus* Tü4 (DSM 12925), *Streptomyces arenae* Tü495 (DSM 40737 and DSM 12134) and *Streptomyces fradiae* Tü27 (DSM 12131).

5. A process for separating epoxide enantiomer mixtures, which comprises
   a) incubating an epoxide enantiomer mixture, which comprises an epoxide hydrolase substrate, with an epoxide hydrolase as claimed in claim 1, a microorganism of the genus *Streptomyces*, an epoxide hydrolase-containing homogenate thereof, or a fraction of this homogenate;
   b) converting the enantiomeric mixture; and
   c) fractionating the reaction mixture.

6. A process as claimed in claim 5, wherein an enantiomeric mixture of an epoxide is converted, which mixture is selected from the group consisting of styrene oxides, 3-phenylg-lycidate, hexane-1,2-oxides, decane-1,2-oxides and indene oxides.

7. The process of claim 5, wherein the conversion of stage (b) is allowed to proceed until reaction equilibrium is established before proceeding to stage (c).

8. A detection method for epoxide hydrolase, which comprises
   a) incubating an analyte in which epoxide hydrolase activity is suspected with an epoxide-containing substrate for the hydrolase under reaction conditions, wherein the analyte is a bacterium of the genus *Streptomyces*, a homogenate therefrom or a fraction of this homogenate;
   b) carrying out a color reaction with the epoxide remaining unreacted in stage a) in the presence of 4-nitrobenzylpyridine (NBP) to form a pigment; and
   c) analyzing the solution from step b) for a decrease in pigment concentration, relative to an epoxide hydrolase-free control solution.

9. A method as claimed in claim 8, wherein the relative decrease in pigment concentration is determined quantitatively and the epoxide hydrolase activity in the analyte is determined therefrom.

10. A method as claimed in claim 8, wherein the epoxide-containing substrate is selected from the group consisting of styrene oxide, 3-phenylglycidate, hexane-1,2-oxide and indene oxide, each of which group members being employed in enantiomeric pure form or as an enantiomeric mixture.

11. A screening method for detecting microorganisms having epoxide hydrolase activity, or having the ability for the enantioselective hydrolysis of epoxides, comprising a detection method as claimed in claim 8.

12. A method for the enantioselective hydrolysis of epoxides, which comprises reacting an enantiomeric mixture of epoxides with an epoxide hydrolase as claimed in claim 1, a microorganism of the genus *Streptomyces*, an epoxide-hydrolase-containing homogenate thereof or a fraction of this homogenate to obtain a reaction mixture comprising non-reacted epoxide and a hydroxyide, and isolating the non-reacted epoxide or the hydroxide, or both from the reaction mixture.

13. A process for producing epoxide hydrolases (E.C. 3.3.2.3), which comprises
   a) producing a cell homogenate from a culture of a microorganism of the genus *Streptomyces*;
   b) fractionating the homogenate obtained in stage a), and testing the resultant fractions for epoxide hydrolase activity; and
   c) combining fractions having epoxide hydrolase activity, and optionally further fractionating the combined fractions.

14. The process of claim 13, wherein the resultant fractions are tested for epoxide hydrolase activity by a method which comprises
   a) incubating an analyte in which epoxide hydrolase activity is suspected with an epoxide-containing substrate for the hydrolase under reaction conditions, wherein the analyte is a bacterium of the genus *Streptomyces*, a homogenate therefrom or a fraction of this homogenate;
   b) carrying out a color reaction with the epoxide remaining unreacted in stage a) in the presence of 4-nitrobenzylpyridine (NBP) to form a pigment; and
   c) analyzing the solution from step b) for a decrease in pigment concentration, relative to an epoxide hydrolase-free control solution.

15. The process of claim 14, wherein the relative decrease in pigment concentration is determined quantitatively and the epoxide hydrolase activity in the analyte is determined therefrom.

16. The process of claim 14, wherein the epoxide-containing substrate is selected from the group consisting of styrene oxide, 3-phenylglycidate, hexane-1,2-oxide and indene oxide, each of which group members being employed in enantiomeric pure form or as an enantiomeric mixture.

17. The process of claim 14, wherein the bacteria of the genus *Streptomyces* are selected from the strains *Streptomyces griseus* (DSM 40236 and DSM 13447), *Streptomyces thermovulgaris* (DSM and 40444 and DSM 13448), *Streptomyces antibioticus* Tü4 (DSM 12925), *Streptomyces arenae* Tü 495 (DSM 40737 and DSM 12134) and *Streptomyces fradiae* Tü27 (DSM 12131).

* * * * *